United States Patent [19]
Rozov et al.

[11] Patent Number: 5,416,244
[45] Date of Patent: May 16, 1995

[54] PREPARATION OF ISOFLURANE

[75] Inventors: Leonid A. Rozov, Fair Lawn; Fernando Quiroz, Elizabeth; Gerald G. Vernice, Nutley, all of N.J.

[73] Assignee: Ohmeda Pharmaceutical Products Division Inc., Liberty Corner, N.J.

[21] Appl. No.: 769,139

[22] Filed: Sep. 30, 1991

[51] Int. Cl.$^6$ ............................................. C07C 41/00
[52] U.S. Cl. ................................. 568/684; 204/157.92
[58] Field of Search ..................... 568/684; 204/157.92

[56] References Cited

U.S. PATENT DOCUMENTS 3,535,388 10/1970 Terrell .
3,535,425 10/1970 Terrell .
4,720,587 3/1973 Croix .

OTHER PUBLICATIONS

Dedek et al., Purification of 2-chloro-1,1,2-trifluoroethyl dufluoronmethyl ether, ca, 06 (1): 4523c, 1986.

Paleta et al.–*J. Fluorine Chemistry*, vol. 39, (1988), pp. 397–414 (I).
Paleta et al.–*Bulletin de La Societe Chimique De France*, vol. 6, (1986), pp. 920–924 (II).
Paleta et al.–*Collection Czechoslovak Chem. Commun.*, vol. 48, (1983), pp. 766–771 (III).

*Primary Examiner*—Johann Richter
*Assistant Examiner*—Rebecca Cook
*Attorney, Agent, or Firm*—R. Hain Swope; Larry R. Cassett

[57] ABSTRACT

An improved process for the production of isoflurane is disclosed. Isoflurane is formed by the exhaustive chlorination of 2,2,2-trifluoroethyl difluoromethyl ether with chlorine gas. The reaction mixture, preferably without purification or refining, is treated with UV light in the presence of isopropanol to reduce 1,1-dichloro-2,2,2-trifluoroethyl difluoromethyl ether, the other major component thereof, to isoflurane. Isoflurane is thereby obtained in yields of at least 80%.

11 Claims, No Drawings

PREPARATION OF ISOFLURANE

The present invention relates to the field of inhalation anesthetics. In particular, this invention is directed to an improved method for preparing the inhalation anesthetic isoflurane which produces a significant increase in yield over present methods.

BACKGROUND OF THE INVENTION

Isoflurane, 1-chloro-2,2,2-trifluoroethyl difluoromethyl ether ($CF_3$—CHCl—O—$CF_2$H), has been the most widely used inhalation anesthetic over the past decade. Isoflurane, its preparation and use, are disclosed in Terrell U.S. Pat. Nos. 3,535,388 and 3,535,425, both issued on Oct. 20, 1970.

A number of preparations of isoflurane have been published. In one synthesis, isoflurane is prepared by the chlorination of 2,2,2-trifluoro-ethyl-difluoromethyl ether ($CF_3$—$CH_2$—O—$CF_2$H). In order to prevent the level of the impurities $CF_3$—$CCl_2$—O—$CF_2$H, $CF_3$—$CH_2$—O—$CF_2$Cl and $CF_3$—CHCl—O—$CF_2$Cl in the reaction mixture from exceeding acceptable levels, i.e. about 10% by weight, the chlorination must be terminated when only about 60% of the starting material, $CF_3$—$CH_2$—O—$CF_2$H, has been consumed. Continued chlorination will produce excessive amounts of the by-product 1,1-dichloro-2,2,2-trifluoroethyl difluoromethyl ether, ($CF_3$—CCl—O—$CF_2$H).

In the above-described synthesis, after termination of chlorination, the reaction mixture comprising isoflurane, the starting material, and the above-mentioned impurities is subjected to fractional distillation. The starting material, $CF_3$—$CH_2$—O—$CF_2$H and $CF_3$—$CH_2$—O—$CF_2$Cl, recovered thereby, are recycled to the chlorination stage.

Heretofore, $CF_3$—$CCl_2$—O—$CF_2$H recovered by the fractional distillation, has been reduced to form isoflurane by a method utilizing metallic zinc and aqueous acetic acid, which is expensive, both in terms of time and equipment. The zinc method has a further disadvantage in that it poses an environment disposal problem due to the formation of $Zn(OCOCH_3)_2$ and $CH_3$—O—$CF_2$—CHCl—O—$CF_2$H.

In accordance with the present invention, the foregoing process is substantially improved in terms of efficiency, cost and environmental disposal problems.

SUMMARY OF THE INVENTION

Isoflurane is prepared by exhaustive chlorination of 2,2,2-trifluoroethyl difluoromethyl ether followed by reduction of the unpurified reaction mixture by ultraviolet light in the presence of isopropanol. Isoflurane is recovered in yields greater than 80% by this process.

DETAILED DESCRIPTION OF THE INVENTION

The present invention affords a significant improvement in the synthesis of isoflurane, 1-chloro-2,2,2-trifluoroethyl difluoromethyl ether $CF_3$—CHCl—O—$CF_2$H, by the chlorination of 2,2,2-trifluoroethyl difluoromethyl ether ($CF_3$—$CH_2$—O—$CF_2$H). Heretofore, this chlorination has been carried out under carefully controlled conditions and terminated when only about 60% of the starting ether had been consumed. In the subject method, the chlorination is carried out to exhaustion of the starting material which is atypical of most chlorination procedures utilizing chlorine gas.

In accordance with the subject invention, chlorine gas is bubbled through the starting material, 2,2,2-trifluoroethyl difluoromethyl ether, at low temperatures, e.g. from 0° to 25° C., preferably from 10° to 15° C., until it is no longer detectable in the reaction mixture. This generally will require not less than about 8 hours, preferably from 8 to 12 hours. The chlorination is carried out under irradiation with light from a suitable source, such as an incandescent lamp.

The reaction mixture at the completion of exhaustive chlorination is a mixture of chlorofluoro ethers typically comprising about 34–37% of flurane, about 54–58% of 1,1-dichloro-2,2,2-trifluoroethyl difluoromethyl ether ($CF_3$—$CCl_2$—O—$CF_2$H), 6–7.5% of 1-chloro-2,2,2-trifluoroethyl chlorodifluoromethyl ether ($CF_3$—CHCl—O—$CF_2$Cl) and 1–2% of 2,2,2-trifluoroethyl chlorodifluoromethyl ether ($CF_3$—$CH_2$—O—$CF_2$Cl).

The present process is particularly advantageous in that the above-described reaction mixture is treated without any purification, preferably in the original vessel, thus eliminating several distillation and transfer steps. It has been found that 1,1-dichloro-2,2,2-trifluoroethyl difluoromethyl ether can be readily reduced to isoflurane by irradiation with ultraviolet light under an inert atmosphere in the presence of isopropanol. The reaction is carried out until 1,1-dichloro-2,2,2-trifluoroethyl difluoromethyl ether is no longer detectable in the reaction mixture.

All other conditions being the same in the above reduction, the rate of reaction is directly influenced by the amount of isopropanol utilized. For example, utilizing an excess of isopropanol, such as a weight ratio of reaction mixture to isopropanol of 1:3, the reaction will be completed in about one hour. Utilizing equal quantities by weight of the reaction mixture and isopropanol, the reaction requires about 3.5 hours to go to completion. These times are based on a reaction mixture of 100 grams. Those skilled in the art will appreciate that larger quantities of reactants as well as light intensity, the configuration of the reaction vessel and the like, may also have an effect on the rate of reaction.

In the subject method, reduction of the reaction mixture as described above, yields, in addition to isoflurane, acetone and HCl. Purified isoflurane can be recovered from the reaction mixture by either of two methods. In a first purification method, the reaction mixture is extracted with water which removes any excess isopropanol, HCl and some acetone. The aqueous phase is treated as waste. The phases are separated, and the organic phase is dried. Isoflurane is recovered from the organic phase by azeotropic distillation with the addition of a relatively small amount of acetone. This method requires a subsequent extractive distillation with water to remove the acetone from the isoflurane.

A preferred purification method is to fractionally distill the reaction mixture to separate the low boiling components, principally acetone, isoflurane and small quantities of dichlorinated ethers. Isoflurane is recovered from the fraction boiling at from about 48° C. to about 76° C. by the sequential steps of azetropic distillation and extractive distillation as described above. The dry isopropanol is recovered for recycle from the bottoms of the fractionation by flash distillation. Flash distillation is utilized to separate isopropanol from trace amounts of pinacol $(CH_3)_2$—C(OH)—C(OH)—$(CH_3)_2$ which is formed in the reaction and which, if allowed to accumulate in the recycle, will inhibit the desired UV reduction. The small amount of pinacol and other by-products remaining after the flash distillation is discarded.

The improved process of this invention provides isoflurane in excellent yields of from 80% to 85% or higher. In the preferred purification method, the unconsumed isopropanol required for the process is recycled into the reduction step. The process can be carried out in a semi-continuous manner by sequentially treating a given quantity of $CF_3$—$CH_2$—O—$CF_2H$ with chlorine gas and in the same reactor, reducing the reaction mixture as described herein. Fractional distillation of the reaction mixture and flash distillation of the bottom fraction therefrom yields a large measure of the isopropanol which can be recycled to a fresh batch of starting material.

The following Examples further illustrate this invention, it being understood that the invention is in no way intended to be limited to the details described therein. In the Examples, all parts and percentages are on a weight basis and all temperatures are in degrees Celsius unless otherwise stated.

EXAMPLE 1

Chlorination of 2,2,2-trifluoroethyl difluoromethyl ether

The reaction was carried out in a 100 ml jacketed glass cylindrical reactor equipped with a magnetic stirring bar, a thermometer, a gas dispersion tube, a dry ice condenser connected to an empty flask and, in turn, to a water scrubber. The reactor was charged with 200 g of 2,2,2-trifluoroethyl difluoromethyl ether and chlorine gas was slowly bubbled therethrough at 10° during which the reaction vessel was irradiated with a 250 watt incandescent light. The introduction of chlorine was continued until analysis showed no starting material remaining in the reaction vessel, 10 hours. The reaction mixture was analyzed at 60-minute intervals by gas chromatography (GC) utilizing a Hewlett-Packard model 5790A analyzer.

The crude reaction mixture weighed 264 g at the conclusion of chlorination and was comprised of, in area percents, 1.4% of $CF_3$—$CH_2$—O—$CF_2Cl$; 35.5% of isoflurane; 56.0% of $CF_3$—$CCl_2$—O—$CF_2H$; and 6.4% of $CF_3$—CHCl—O—$CF_2Cl$.

EXAMPLE 2

Reduction of 1,1-Dichloro-2,2,2-trifluoroethyl difluoromethyl ether

This experiment was carried out in a one liter Pyrex, 3-neck flask equipped with a magnetic stirrer, a gas introduction tube and a dry ice condenser connected to a trap (−78°). Three hundred grams of isopropanol was introduced into the reaction flask and 100 g of the crude mixture formed in Example 1 was added thereto without purification.

The reaction mixture was irradiated for 1 hour at 10 cm distance at room temperature with a 450 watt medium pressure mercury ultraviolet lamp. During irradiation, a low flow (10 ml/min) of nitrogen was maintained into the reaction vessel. At the end of 1 hour, there was no discernible $CF_3$—$CCl_2$—O—$CF_2H$ in the reaction mixture.

A total of 300 milliliters of water was added to the reaction mixture, and it was steam distilled. The organic layer was recovered with a Dean-Stark trap and washed with ice-cold water to remove traces of isopropanol.

Analysis of the organic layer (81.2 g) was as follows:

| | |
|---|---|
| $CF_3$—$CH_2$—O—$CF_2Cl$ | 1.1% |
| Isoflurane | 86.5% |
| $CF_3$—CHCl—O—$CF_2Cl$ | 6.7% |
| Acetone | 4.9% |

The yield of isoflurane, based on GC area percent analysis, was 85%.

The experiment was repeated utilizing equal weight quantities of the reaction mixture and isopropanol. Irradiation as above required 3.5 hours. The yield was also 85%.

EXAMPLE 3

Reduction of 1,1-Dichloro-2,2,2-trifluoroethyl difluoromethyl ether using isopropanol recycle A crude mixture (100 g) of chlorinated ethers, such as described in Example 1, and 300 g of isopropanol were irradiated for 1 hour as described in Example 2. The reaction mixture was distilled using a 1-foot column packed with 2 mm glass beads. A fraction boiling between 48° and 76° was collected. The remainder in the reaction vessel was flash distilled to provide 240 g of isopropanol.

A second 100 g of chlorinated ether mixture was admitted to the reaction vessel along with the 240 g of isopropanol recovered above and 60 g of fresh isopropanol. Irradiation was resumed and was complete after 3.5 hours. The products were separated, and the crude remainder treated as before. There was obtained 280 g of isopropanol.

A third 100 g of crude chlorinated ethers was added to the reaction vessel along with the 280 g of isopropanol obtained above and 20 g of fresh isopropanol. Irradiation was again resumed and was completed after 5 hours. The product was recovered as above and the 3 fractions boiling at 48°–76° were combined and treated as in Example 2.

The composition of the combined mixtures after treatment (233.1 g) was as follows (area percent):

| | |
|---|---|
| $CF_3$—$CH_2$—O—$CF_2Cl$ | 1.1% |
| Isoflurane | 86.4% |
| $CF_3$—CHCl—O—$CF_2Cl$ | 6.6% |
| Acetone | 5.1%. |

Overall charge of chloroethers—300 g.
Overall charge of isopropanol—380 g.
Overall yield of isoflurane—81%.

We claim:
1. A process for the preparation of isoflurane comprising:
 (a) reacting 2,2,2-trifluoroethyl difluoromethyl ether with chlorine gas to form a mixture of chlorofluoro ethers, predominately isoflurane and 1,1-dichloro-2,2,2-trifluoroethyl difluoromethyl ether, said reaction being carried out until the starting material is exhausted from the mixture;
 (b) reacting said mixture with ultraviolet light in the presence of isopropanol to reduce 1,1-dichloro-2,2,2-trifluoroethyl difluoromethyl ether to isoflurane; and

(c) recovering isoflurane from said mixture.

2. A process in accordance with claim 1, wherein the weight ratio of said mixture to isopropanol is from about 1:1 to 1:3.

3. A process in accordance with claim 2, wherein the weight ratio of said mixture to isopropanol is about 1:3.

4. A process in accordance with claim 1, wherein said reaction in step (b) is carried out at ambient temperature under a nitrogen atmosphere.

5. A process in accordance with claim 1, wherein step (b) is carried out on the mixture formed in step (a) without purification thereof.

6. A process in accordance with claim 5, wherein steps (a) and (b) are carried out sequentially in the same reaction vessel.

7. A process in accordance with claim 1, wherein isoflurane is recovered by fractional distillation of the mixture formed in step (b).

8. A process in accordance with claim 7, additionally including the steps of treating the fraction boiling at from about 48° C. to about 76° C. in said distillation by sequential azeotropic distillation and extractive distillation to recover isoflurane therefrom.

9. A process in accordance with claim 8, additionally including the steps of recovering isopropanol from the bottoms fraction of the fractional distillation and recycling it to step (b).

10. A process in accordance with claim 9, wherein isopropanol is recovered by flash distillation.

11. A process in accordance with claim 1, wherein isoflurane is recovered by treating the mixture formed in step (b) with water thereby forming an organic phase and an aqueous phase, separating said phases and sequentially treating the organic phase by azeotropic distillation and extractive distillation.

* * * * *